US00PP19081P3

(12) United States Plant Patent
Korlipara

(10) Patent No.: US PP19,081 P3
(45) Date of Patent: Aug. 5, 2008

(54) ***COREOPSIS* PLANT NAMED 'RP #4'**

(50) Latin Name: *Coreopsis*
Varietal Denomination: RP #4

(75) Inventor: Harini Korlipara, Canby, OR (US)

(73) Assignees: Terra Nova Nurseries, Inc., Canby, OR (US); The Ivy Farm, Locustville, VA (US)

( * ) Notice: Subject to any disclaimer, the term of this patent is extended or adjusted under 35 U.S.C. 154(b) by 129 days.

(21) Appl. No.: 11/592,083

(22) Filed: Nov. 1, 2006

(65) Prior Publication Data

US 2008/0134387 P1 Jun. 5, 2008

(51) Int. Cl.
*A01H 5/00* (2006.01)

(52) U.S. Cl. ..... Plt./417

(58) Field of Classification Search ..... Plt./417
See application file for complete search history.

*Primary Examiner*—Kent L Bell
(74) *Attorney, Agent, or Firm*—Klarquist Sparkman, LLP

(57) ABSTRACT

A new and distinct *Coreopsis* plant named 'RP #4' characterized by very free flowering rusty yellow colored, daisy-like flowers, a low mounding habit, and excellent vigor.

1 Drawing Sheet

Figure 1:
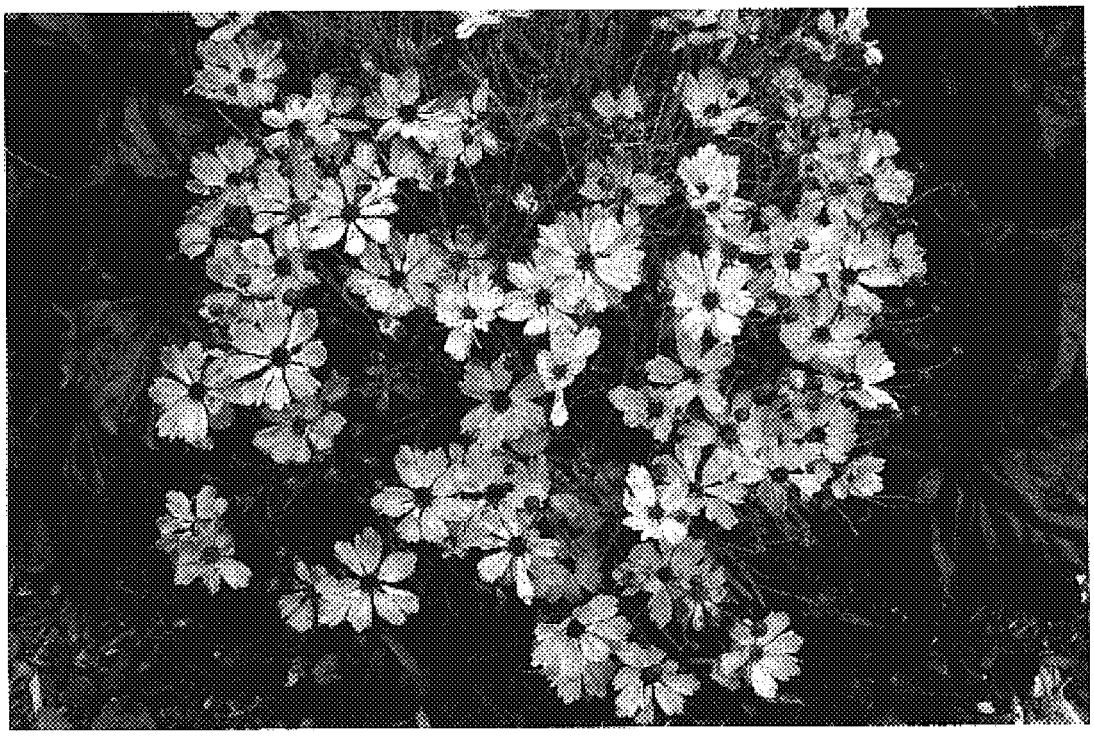

Botanical designation: *Coreopsis* hybrid (of unknown origin).
Variety denomination: 'RP #4'.

BACKGROUND OF THE INVENTION

The present invention relates to a new and distinct plant of *Coreopsis* and given the cultivar name 'RP #4'. *Coreopsis* is in the family Asteraceae. This new cultivar originated as a tissue culture mutation from *Coreopsis* 'Rum Punch' (U.S. Plant patent application Ser. No. 11/488,815). 'RP #4' was one of several interesting mutations found from tissue cultured plants.

SUMMARY OF THE INVENTION

The following traits have been repeatedly observed and are determined to be the unique characteristics of 'RP #4'. These characteristics in combination distinguish 'RP #4' as a new and distinct cultivar:

1. Unique rusty-yellow daisy-like inflorescences.
2. Low, mounding habit.
3. Very free flowering.
4. Excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a one year old *Coreopsis* 'RP #4' growing in the ground in the garden in full sun in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the trial fields in August in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial, grown as an annual.
- *Hardiness.*—USDA Zone 9–10.
- *Size.*—45 cm wide and 30 cm tall to top of inflorescences.
- *Form.*—Low mound with freely branching stems.
- *Vigor.*—Excellent.
- *Roots.*—Fibrous, freely branching, fine, and Yellow White 158A; roots develop easily from stem cuttings.

Stem:
- *Type.*—Ascending.
- *Size.*—30 cm tall and 1 to 4 mm wide.
- *Internode length.*—1.5 to 5.5 cm.
- *Surface.*—Glabrous.
- *Color.*—Green 147B.

Leaf:
- *Type.*—Simple.
- *Shape.*—Mostly linear with some basal leaves with one to two linear side lobes, side lobe(s) perpendicular to main lobe, reflexed.
- *Arrangement.*—Opposite.
- *Size.*—Grows to 5.5 cm long and 2.5 mm wide when linear, side lobe(s) from near base or leaf, grow to 22 mm long and 1 mm wide.
- *Margins.*—Entire.
- *Apex.*—Acute.
- *Base.*—Clasping.

*Surface texture.*—Glabrous on both sides.

*Venation.*—Pinnate.

*Color.*—Top side — Green 147A. Bottom — Green 148B.

Immature inflorescence: Globular, 6 mm wide and 6 mm deep, Greyed Purple 185A on tip and seams with Greyed Orange 175A in the middle and the bottom Yellow Green 147D.

Inflorescence:

*Type.*—Long stalked terminal heads of daisy type inflorescences.

*Peduncle.*—Grows to 8.5 cm tall and 0.5 mm wide, glabrous, Green 137A.

*Size.*—3.5 cm wide and 8 mm deep.

*Ray florets.*—8 in number, no pistil or stamen, obovate, the tip is three to four lobed with the terminal 2 lobes the longest, margins entire, base cuneate, grows to 17 mm long and 9 mm wide, glabrous on both surfaces, 3 mm claw at base, laminae with linear appendage (1 or 2) on side and/or opposite and upright, 10 mm long. Color: Ray floret, topside — somewhat variable, sometimes Greyed Orange 167A darkening to 172B near the tip, others are Greyed Orange 163A; both with Greyed Orange 163B at base; older ray florets turn mustard yellow, Greyed Orange 163B overall. Ray floret, bottom side — Yellow 11B with blotches of Greyed Orange 176A near the tips on some of the ray florets.

*Cone.*—Conic in shape, grows to 6 mm wide and 3 mm deep, Greyed Purple 187A.

*Disc florets.*—Corolla — 3 mm long and less than 1 mm wide, tubular, 4 lobed, Greyed Purple 187A on the lobes to Yellow 11A on tube inside and out, glabrous. Pistil — 5 mm long, 2-branched stigma extruding from the corolla, style 3.5 mm long, Orange 17A overall, ovary 1.5 mm long, White 155A. Stamen — 4, filaments 3 mm long, extruding, Black 202A, pollen Orange 17A.

*Phyllaries.*—In 2 series, series closest to ray florets 8 in number, ovate, entire, acuminate, lobes 6 mm long and 3 mm wide, glabrous, Greyed Orange 167A on top half and Yellow Green 147A on bottom half; lower series 8 in number, lobes 2 mm long and 1.5 mm wide at the base, ovate, entire, acute, glabrous, Yellow Green 147A.

*Bloom period.*—June through September in Canby, Oreg.

*Fragrance.*—Light, daisy like.

Seed: None produced.

*Fertility.*—Infertile.

Disease and pests: *Coreopsis* are susceptible to mildew and fungal spots. No known resistances on the new cultivar.

COMPARISONS TO SIMILAR *COREOPSIS*

Compared to *Coreopsis* 'Limerock Ruby' (U.S. Plant Pat. No. 15,455), this new cultivar has a new and unique flower color of rusty yellow rather than rose pink.

Compared to *Coreopsis* 'Rum Punch' (U.S. Plant patent application Ser. No. 11/488,815), the new cultivar has flowers of a rusty yellow color rather than orangey rose.

Compared to *Coreopsis* 'RP #5', U.S. Plant Pat. No. 18,475, *Coreopsis* 'RP #4' has rusty yellow flower color rather than rust orange.

I claim:

1. A new and distinct *Coreopsis* plant as herein illustrated and described.

* * * * *

UNITED STATES PATENT AND TRADEMARK OFFICE

CERTIFICATE OF CORRECTION

PATENT NO. : PP 19,081 P3
APPLICATION NO. : 11/592083
DATED : August 5, 2008
INVENTOR(S) : Harini Korlipara It is certified that error appears in the above-identified patent and that said Letters Patent is hereby corrected as shown below:

In the Specification:

Column 1, line 5, the following paragraph and heading should be added:

CROSS REFERENCE TO RELATED APPLICATIONS

The present application is related to United States Plant Patent Application Serial Number 11/488,815, directed to a Coreopsis plant named 'Rum Punch'; United States Plant Patent Number 18,502, directed to a Coreopsis plant named 'RP #1'; and United States Plant Patent No. 18,475, directed to a Coreopsis plant named 'RP #5'.

Signed and Sealed this

Twentieth Day of January, 2009

JON W. DUDAS
*Director of the United States Patent and Trademark Office*